United States Patent [19]

Ko

[11] Patent Number: 5,484,609

[45] Date of Patent: Jan. 16, 1996

[54] THERAPEUTIC COMPOSITIONS AND METHODS

[75] Inventor: Thomas S. Y. Ko, South Belgrave, Australia

[73] Assignee: Enzacor Properties Limited, St. Helier, Channel Islands

[21] Appl. No.: 185,061

[22] Filed: Jan. 21, 1994

Related U.S. Application Data

[63] Continuation of PCT/AU92/00371, Jul. 23, 1992.

[30] Foreign Application Priority Data

Jul. 24, 1991 [AU] Australia ................................ PK7398

[51] Int. Cl.$^6$ ............................ A61K 9/26; A61K 38/00; A01N 37/18
[52] U.S. Cl. ........................ 424/470; 424/78.01; 424/474; 424/490; 424/491; 424/497; 514/2; 514/867; 514/885; 514/964; 514/965
[58] Field of Search ................................... 424/470, 474, 424/78.01, 490, 491, 597; 514/964, 965, 867, 885, 2

[56] References Cited

U.S. PATENT DOCUMENTS

| | | | |
|---|---|---|---|
| 3,946,110 | 3/1976 | Hill | 424/470 |
| 4,009,076 | 2/1977 | Green et al. | 195/63 |
| 4,014,334 | 3/1977 | Theeuwes et al. | 424/470 |
| 4,299,613 | 11/1981 | Cardarelli | 71/64 F |
| 4,400,374 | 8/1983 | Cardarelli | 424/78 |
| 4,432,968 | 2/1984 | Page et al. | 424/78 |
| 4,629,621 | 12/1986 | Snipes | 428/402.24 |
| 4,744,976 | 5/1988 | Snipes et al. | 424/493 |

FOREIGN PATENT DOCUMENTS

| | | |
|---|---|---|
| 623036 | 3/1991 | Australia . |
| 0091767 | 10/1983 | European Pat. Off. . |
| 56-059707 | 5/1981 | Japan . |

*Primary Examiner*—Ronald W. Griffin
*Attorney, Agent, or Firm*—Christensen, O'Connor, Johnson & Kindness

[57] ABSTRACT

Compositions comprising (i) granules comprising a biologically active material in association with a weak base and partially coated with a delayed release material soluble in intestinal juice, (ii) an acidifying agent having a pH between 1.5 to 6, and (iii) a gel forming agent are described. There is also described a composition comprising an acidic gel having a pH between 1.5 to 6 and containing microgranules comprising a biologically active material in association with a weak base and partially coated with a delayed release material soluble in intestinal juice. The compositions may be used in the treatment of diseases associated with intestinal pathogens in animals. Where the biologically active material is a protease, receptor/adhesion sites in the intestines for pathogens may be proteolysed so as to prevent pathogen binding to intestinal surfaces.

38 Claims, No Drawings

THERAPEUTIC COMPOSITIONS AND METHODS

This application is a continuation of international application No. PCT/AU92/00371, filed Jul. 23, 1992.

This invention relates to novel compositions, to methods for the delivery of biologically active substances to the small intestinal tract, and to methods for the treatment of intestinal pathogens in animals.

The small intestinal tract of animals, is important for the adsorption of biologically active materials such as digested food components, antibiotics, vitamins, etc.

Biologically active materials are often acid labile and thus may be degraded or inactivated on passage through the stomach on route to the small intestine for absorption or bio-activity.

It has previously been proposed to enteric coat materials with acid resistant/alkali soluble agents such as cellulose acetate phthalate, so that biological materials pass safely through the stomach for subsequent liberation in the intestines. In young animals, for example young piglets, the passage time of enterically coated materials through the intestines may be so rapid that the enteric coating fails to break down, resulting in excretion of the enterically coated materials, or the liberation of the biologically active materials in inappropriate regions of the intestine such as the large intestine.

Additionally, biologically active material such as proteases may be unpalatable and may cause irritation and inflammation of the buccal cavity and oesophagus.

A requirement exists for compositions and methods which effectively and conveniently facilitate the delivery of biologically active material to the intestinal regions of animals, In accordance with one aspect of this invention there is provided a composition which comprises:

(i) granules comprising a biologically active material in association with a weak base and partially coated with a delayed release material soluble in intestinal juice;

(ii) an acidifying agent having a pH between 1.5 to 6 when in solution: and (iii) a gel forming agent.

In accordance with another aspect of this invention, there is provided a composition comprising an acidic gel having a pH between about 1.5 to about 6, and containing microgranules comprising a protein in association with a weak base and partially coated with a delayed release material soluble in intestinal juice.

The biologically active material may be a protein such as an enzyme, growth factor, cytokine or hormone. Where the enzyme is a proeolytic enzyme, it is preferably selected from bromelin, papain, ficin, chynotrypsin, trypsin, ribonuclease, carboxypeptidase A or B, or subtilisin. Bromelin is most preferred. Growth factors include growth hormone, insulin and the like.

As used herein the term protein also includes peptides within its scope. Generally, a peptide comprises from 2 to 100 amino acids, and a protein comprises 100 or more amino acids.

Biologically active materials may be non-proteinaceous and may include vitamins, co-factors, metal ions, antibiotics or the like.

Biologically active materials are generally provided in fine particulate form, such as in %he form of powders.

By the term "weak base" is meant an alkalyzing agent such as dicalcium phosphate, calcium carbonate, calcium bicarbonate, aluminium hydroxide, sodium bicarbonate and the like. Advantageously, the weak base is sparingly soluble. The weak base is generally provided in fine particulate form, for dissolution in appropriate media such as stomach juices. The weak base and biologically active material may be admixed together when both are in particulate form, prior to coating.

Granules may be formed by partially coating mixtures of biologically active materials and buffering agents in particulate form, with a delayed release material (otherwise known as an enteric coating) soluble in intestinal juices. Fluidized particles may be spray coated with a solution of the delayed release material. The size of granules formed by spray coating fluidized particles (in a fluidized bed) can be controlled, and is dependant on the velocity of particle flow and spray pressure of the coating solution. For example, fast granule flow and high spray pressure leads to small granules. Without limiting this invention, granules usually have a diameter between 50 to 500 µm. These granules may be referred to as microgranules.

In accordance with this invention, granules are only partially coated with delayed release material. This is an important aspect of this invention, as it allows rapid release of biologically active material in the intestine. Partial coating may be generally achieved utilizing spray coating of fluidized material. The extent of coating can be determined by microscopic analysis of granules. Generally, from 10 to 90% of the surface area of the granules is coated with the delayed release material. Preferably, from 50 to 80% of the granule surface is coated with delayed release material.

Delayed release materials are any materials which are substantially impermeable and maintain their integrity below about pH 6.0, and which degrade, dissolve, become permeable or lose their structural integrity at alkaline pH, from about pH 7.0 upwards. Examples of such materials include cellulose acetate phthalate, other Types of enteric coatings, and the like.

Acidifying agents may be provided in particulate form, and on solubilization in aqueous solution have a pH between about 1.5 to about 6, preferably about 3.5 to about 6. Any non-oxic agent which satisfies this criteria is within the scope of the present invention. Examples of acidifying agents are citric acid, lactic acid, Tartaric acid, succinic acid, oxalic acid, fumaric acid, butyric acid, hydrochloric acid, proprionic acid and the like.

Gel forming agents are also generally provided in particulate form and are capable of forming a gel matrix under appropriate conditions, such as dispersion or mixture with an aqueous or organic solution (such as glycerine or polyethylene glycol). Examples of gel forming agents include karageenans, alginates, polyvinyl pyrollidone (PVP), methyl methacrylate substituted with bile-soluble fatty acids, dextran, and the like. An acidic gel is formed by hydrating or dispersing a gel matrix in an acidic solution or in The presence of an acidifying agent as herein described.

The composition of one aspect of this invention is provided in particulate form, as a mixture of granules with a particulate acidifying agent and a gel forming agent. In this form, the composition may be readily sored and transported. When desired to be used for delivering biologically active material to the intestinal regions of an animal, a small amount of water or other non-toxic solution is added o the composition to give an acidic gel (formed by the transition of the gel forming agent to a gel, in the presence of the acidifying agent) having microgranules contained therein. This procedure is followed for he production of the acidic gel composition as described herein.

The ratio of components (i)–(iii) of the composition of this invention is generally unimportant, but may, for example, be in the ratio of 10:1:1 calculated on a w/w basis. Similarly, The ratio of biologically active material to buffering agent is not important, but, for example, may be in the ratio 1:4 (w/w).

The composition in accordance with this invention may additionally comprise one or more antibiotics. Where a composition according to an embodiment of this invention is in granular form, the antibiotic may be in the form of a powder or granules which is admixed with the other components. When a composition according to an embodiment of this invention is in the form of a gel, the one or more antibiotics are generally dissolved during preparation of the gel matrix and therefore generally distributed throughout the gel matrix.

Any known class of antibiotics may be used in the compositions of this invention, and include, for example, one or more antibiotics selected from penacillin, cephalosporin, eryhromycin, tetracycline, thienamycin, neomycin, and the like, such as derivatives thereof having antibiotic activity.

As will be described hereinafter, it is believed that antibiotics interact synergistically with the compositions of this invention as described hereinbefore, particularly when the biologically active material is a protease, in the treatment of intestinal bacterial infections associated with various disease states.

In still another form of this invention there is provided a method for the delivery of a biologically active substance to the upper small intestinal tract of an animal which comprises administering to the animal a composition as described herein. Where the composition is a gel, it is directly administered to an animal. Where the composition is in particulate form, it is first dispersed or mixed with an appropriate solution to form a gel and then administered to an animal.

In yet another form of this invention there is provided a method for the treatment of intestinal pathogens and/or diseases associated with intestinal pathogen infection in animals which comprises orally administering to an animal a therapeutically effective amount of a composition as previously defined herein. Preferably, the composition contains a protease, for example bromelin, optionally is in association with one or more antibiotics. In an alternative embodiment one or more antibiotics may be administered contemporaneously or substantially contemporaneously.

Intestinal pathogens which may be treated in accordance with this invention include bacteria, viruses or parasites. Examples of such pathogens include, for example, enterotoxigenic *Escherichia coli* Shigella, Yersinia, Pleisiomonas, Vibrios, Aeromonas, Campylobacter, rotavirus, Cryptosporidia or Coccidosis.

The invention further relates to a method for the treatment of diarrhoea in an animal which comprises administering to the animal a composition comprising an acidic gel having a pH between 1.5 to 6, said gel containing microgranules which comprise a proteolytic enzyme in association with a weak base and partially coated with a delayed release material soluble in intestinal juice. Optionally the composition may comprise one or more antibiotics, or one or more antibiotics may be administered contemporaneously or substantially contemporaneously.

Any animal, preferably a mammal such as humans, pigs, cattle, horses, sheep, birds, fish, or crustaceans may be treated in accordance with the methods of this invention. Particularly, the animal is a monogastrate as a pig or human infant, or an immature ruminant such as a calf.

While this invention in its various embodiments has particular application to monogastrate and immature ruminant animals, the invention also has applications in aquaculture in he treatment of intestinal diseases which effect fish and crustaceans (which may, for example, be intensively raised in ponds, tanks and the like). Compositions containing proteases would act to remove adhesion sites in the intestines of fish and crustaceans for pathogens, as well as providing a systemic immunity effect.

In respect of humans, the composition of this invention may be mixed in a drink such as water or a buffered solution having a pH of about 4 to 7. The extent of coating of the microgranules for human administration is generally in the order of about 20%.

The oral administration of an acidic gel in accordance with this invention may be effected by any convenient means. For example, the gel may be poured or injected into the Duccal cavity of an animal. Alternatively, The gel may be applied to or mixed with food, such as animal feed.

The amount of acidic gel administered to an animal for the delivery of a biologically active substance to the intestinal regions of animals, or for the treatment of diarrhoea, is generally unimportant, as is the frequency of administration, and will depend on factors such as the weight and health of the animal, its nutritional status the condition being treated and like factors, and will generally be determined by a farmer or veterinarian or physician. By way of example only, a piglet may be administered 1 to 5 ml of an acidic gel by way of syringe into the buccal cavity. Again, by way of example, an effective amount of the composition of this invention may be from about 0.01 g/kg body weight about 5 g/kg body weight The effective delivery of biologically active proteases to the upper small intestinal tract utilizing the compositions of this invention, has been shown by the inventors To result in the destruction (presumably by proteolysis) of intestinal membrane receptors for pathogens (such as receptors for The pathogenic bacteria *E. coli* K88) and The destruction of toxin receptors in the intestines. The protease containing compositions of this invention limit the natural physiology of the body by using digestive enzymes to temporarily remove bacterial and other pathopen receptors from the surface lining of the post intestinal surface. Without these receptors, pathogenic organisms cannot colonise on the surface of the gut lining. Without colonisation in large numbers, pathogenic microbes cannot generate disease. This unique action in preventing microbial disease by modifying the host and no the pathopen overcomes the traditional disadvantage of anibiotics, that being microbial antibiotic resistance.

Additionally, and surprisingly, compositions of this invention are effective against pathogenic microbes that may not possess a recognised adhesive mechanism or receptor (such as protozoan parasites, and viruses such as rotavirus and transmissible gastroenteritis virus (TGE)). This latter effect indicates that the compositions of this invention, particularly those containing proteases (such as plant and animal proteases, for example, bromelin, papain, ficin, chymotrypsin, trypsin, ribonuclease, subtilisin, carboxypeptidase A or B, and the like), may act as non-specific immuno stimulant. The immuno-stimulant effect of the compositions of this invention is not well understood. While this immuno-stimulation may be specific for a particular pathopen it is believed to be non-specific and involving The increased production of IgG.

The combination of a protease containing composition as referred to herein with antibiotics may offer a synergistic effect in the treatment of intestinal microbial infections. This synergistic interaction may arise because of the non-specific action in elevating antibody response as mentioned above, which compliments the antimicrobial action of antibiotics. It has also surprisingly been found that the above mentioned compositions containing a protease and an antibiotic increase antibioic systemic absorption from the intestinal regions. The mechanism behind this effect is unclear. This effect is also present when anibiotics are administered contemporaneously or substantially contemporaneously with the acidic gel composition of an embodiment of this invention.

Protease containing compositions of this invention also provide broad spectrum anti-diarrhoeal effects, weight gain, and a reduction in mortality on administration to animals, particularly in immature monogastrates such as pigs.

In accordance with another aspect of this invention there is provided a method for the non-stimulation of the immune system in animals, which method comprises orally administering to an animal a composition comprising an acidic gel having a pH between about 1.5 to about 6, and containing microgranules containing a biologically active material, particularly a protease, in association with a weak base and partially coated with a delayed release material soluble in intestinal juice. The protease may be of animal or plant origin, and selected, for example, from proteases such as bromelin, papain, ficin, chymotrypsin, trypsin, ribonuclease, carboxypeptidate A or B, or subilisin and the like.

As will be apparent from the Examples hereafter, protease containing compositions of this invention cause a significant decrease in pathogenic intestinal flora. This unexpected phenomenon provides the opportunity to recolonise an animal's intestine with non-pathogenic advantageous bacteria, such as lactobacilli, streptococci and the like from healthy animals.

In accordance with an aspect of this invention there is provided a method which comprises The steps of orally administering to an animal a composition comprising an acidic gel having a pH between about 1.5 to about 6 and containing microgranules comprising a protease in association with a weak base and partially coated with delayed release material soluble in intestinal juice, and thereafter orally administering to said animal microorganisms which organisms may comprise one or more components of the intestinal flora of healthy animals.

The organisms administered to an animal in this aspect of the invention may be referred to as "probiotics" and may be administered at The same time as The acidic gel composition or shortly thereafter, such as from several minutes to 24 hours.

Probiotics may be administered in the form of freeze dried organisms or other convenient form, such as in the form of a nutrient solution, slurry of microorganisms and the like.

In yet another aspect of This invention there is provided an acidic gel or particulate composition as described herein in admixture with conventional animal feeds as are well known in the art, such as pelleted feed, weaner pellets or the like.

The various features of the composition of this invention are particularly advantageous for the following reasons: 1. The provision of granules of small particle size, namely 50 μm o 500 μm, as provided herein (these may be referred to as "microgranules") delay release of material in %he buccal cavity (thus protecting he buccal cavity from he effects of proteases such as bromelin), and the stomach. Small particle size also facilitates gastric passage.

2. The provision of buffering within the granule in the pH range 3 to 6 acts to inhibit the proteolytic activity of pepsin in the stomach, neutralise stomach pH, inhibit inactivation of acid-sensitive biological materials such as proteases, and enable the pH optimum of a biological material, such as the proteolytic enzyme bromelin to be maintained.

3. The partial coating of granules with a delayed release material protects biological material from acid inactivation, and enables gradual release of biological material within the small intestine, starting in the duodenum, as well as masking taste. Fully enteric coated granules may not liberate biological material, particularly in immature monogastrates or ruminants, and thus may be excreted, or contents liberated at an inappropriate site in the intestine. Unexpectedly, a partial coating of delayed release material does not lead to inactivation of biologically active agents in the stomach. This is presumably due to the presence of the buffering set out in point (2) above.

4. The acidifying agent promotes animal salivation and increases palatability, as well as lowering gastric pH and thereby maintaining the integrity of the delayed release material in the stomach.

5. When in the form of a gel, the gel-forming agent reduces diffusion from the granules and keeps the granules in an easily flowing suspension. Protection of buccal mucosa is also provided by the gel which helps restrict diffusion of free enzyme (or other biological material) from the granules. Due to the presence of an acidifying agent in the gel, salivation and palatability are promoted.

This invention will now be described, by way of example only, with reference to the following non-limiting examples.

EXAMPLE 1

Preparation of compositions:

The following composition containing the proteolytic enzyme bromelin was prepared:

| (i) Granule: | |
|---|---|
| Bromelin | 25% w/w |
| Dicalcium phosphate | 65% w/w |
| Cellulose acetate phthalate | 10% w/w |
| | 100% w/w |

(ii) Acidifying agent:
   Citric acid 5% w/w relative to granule weight
(iii) Gel forming agent:
   Carboxymethyl cellulose 10% w/w relative to granule weight Method:

1 Disperse 1 kg of cellulose acetate phthalate into 10 liters of water,

2 Add q.s. sodium carbonate or sodium hydroxide to the solution of step 1 to give sodium cellulose acetate phthalate (sodium CAP) at approx, pH 6,5, 3 Weigh out bromelin (2,5 kg) and dicalcium phosphate (6.5 kg) and discharge into the spray coating container in the Glatt (trademark) or Aeromatic (trademark) spray coating apparatus, The powder is fluidized and heated to 50° C., 4 Spray the sodium CAP onto the fluidized powder at a pressure of 2 bars until complete and then allow to dry for 30 minutes, 5 The partially coated material is then blended with citric acid (0.6 kg) and carboxy methyl cellulose (1 kg) using a standard blending device, It is the spray coating of fluidized particles which is particularly amenable to the production of partially coated granules. In order to achieve partial coating the ratio (w/w) of biologically active material/weak base to coating is generally about 1:0.1 or 1:<0.1.

The resulting granular composition is referred to in the subsequent Examples as "Detach", A 5 ml "dose" of Detach is prepared by adding water (about 4 ml) to 1 g (approximately 1 ml volume) of granules to give a 5 ml gel volume.

EXAMPLE 2

Determination of the intestinal transit time of bromelin administered as a single 5ml dose of Detach which contains 1 g of granules to which waer is added to give an acid gel base.

Eighteen unweaned piglets, 4 weeks old, were ramked on a live weight basis and allocated in a random manner into Detach treated and untreated (control) groups in the ratio of two treated piglets to one control piglet. Piglets were fed artificial milk (500ml each) twice each day.

At the commencement of the experiment all piglets in the Detach treated group were orally dosed with a standard 5ml dose of Detach (a suspension containing 1 g of granules dissolved in water to give an acid gel base). A period of 1h, 12h, 28h, 48h, 72h and 144h post inoculation, randomly selected groups of three piglets (two treated, one control) were killed by barbiturate overdose and the small intestine removed. Sections (10cm long) of the intestine from 5 sites: duodenal, lower ileal, mid jejunal and midway between these sites were removed and immediately stored at $-20°$ C.

On completion of the experiment, the intestinal sections from each pig were thawed, opened longitudinally and the mucosal surface scraped with a glass slide. Mucosal scrapings (0.2 g) were suspended in 1.8 ml of working dilution buffer (WDB) consisting of phosphate buffered saline (PBS, 0.1 M, pH 7.2) to which Tween 30 (0.05% v/v), bovine serum albumin (BSA, 0.25% w/v), ethylene diamine tetraacedtic acid (EDTA<1mM) and sodium azide (0.1% w/v) had been added. The scraping suspensions were then tested for the presence of bromelain by enzyme immuno assay (EIA, procedure 1 set out below). Sensitivity of this assay had previously been established as 3ng when the same batch of enzyme as in the Detach, bu suspended in phosphate buffered saline, was tested by titration. Residual bromelain from the Detach doses were evident in all intestinal sites of treated piglets killed at 1h and 12h after dosing. Bromelain was evident in one piglet (site 4 and 5 only) killed 28h after dosing. No intestinal material taken from control piglets reacted in the EIA, nor did material from any piglets killed at 48 h or longer after dosing.

Conclusion:

Transit time of bromelin through the piglet small intestine is similar to that of other foodstuffs. Bromelin is readily released into the intestine.

Procedure 1:

Enzyme immunoassay for Bromelin:

Plates: Nunc. (Trademark)

Plate Coating: Anti bromelin IgG raised in rabbits. coated 2h/37° C. in carbonate: bicarbonate buffer (0.05 M, pH 9.6) containing 10 µg/ml IgG) 100 µl/well. Stored at 4° C. until required.

Test Samples: Intestinal scrapings diluted 1:10 w/v in working dilution buffer (WDB, described earlier). Incubated for 30 min a 37° C.

Conjugate: Avid in urease (Allelix Inc., Mississaugu, Toronto, Canada) 1:400 v/v in conjugate buffer (Chandler, D.S. et al., Vet Microbiol. 11: 153–161, 1986). Incubated for 30 min. at 37° C.

Substrate: Urease substrate solution (CSL; Parkville). Read at 540 nm (approximate).

EXAMPLE 3

Effect of DeTach on intestinal K88 receptor activity.

The *E. coli* K88 receptor is typical of a number of protein or glycoprotein receptor molecules that have been demonstrated to play critical roles in the pahogenesis of important microbiological diseases of the small intestine. Receptors located on the intestinal brush border membrane have been shown to be involved in attachment (colonisation), cell entry and toxin delivery by intestinal pathogens. At least some of these receptors, including the K88 receptor, have been demonstrated to be readily inactivated by proteolytic enzymes, including those proteases that are normally active in the small intestine (Wellwood, R., Biochim, Biophys. Acta 632: 326–335, 1980; Staley, T. E. and Wilson, J. B., Mol.. Cell. Biochem 52: 177–189, 1983; Mouricourt, M. A. and Julien R. A., Infect. Immun., 55: 1216–1233, 1987).

Piglets were fitted with a "Y" shaped stainless steel illeal fistula 7 to 14 days after birth.

Piglets were reared in weaner flat-deck accommodation and were maintained in a diet of reconstituted milk until at least 4 weeks of age.

K88 receptor activity was estimated by enzyme immunoassay (Chandler 1986, Supra, subsequently designated KPEIA). Intestinal samples were collected into at least 10% v/v WDB to which 0.1% w/v TI had been added. This buffer was designated WDB/TI.

A continuous sampling procedure was employed. This procedure consisted of connecting a teflon tube (4 mm bore) to the threaded end of the fistula and passing the other end of the tube through a slow running (0.5–1.0 ml/min) peristaltic pump to the sample tube. These tubes contained 1 ml of WDB/TI and were housed in a fraction collector of the type used to monitor chromatography columns in protein chemistry (Frac 100, Pharmacia). Ice was placed in the bowl that surrounded the rack of tubes at the start of each day. Each tube collected the output of the pump over 10 minute period. In order to reduce the amount of drag on the fistula during sampling, the weight of the tube between the pig and the pump (placed over the pens)was suspended in a counterbalanced line.

Detach treatment:

Piglets were sampled over a 24–48 h period prior to Detach medication in order to obtain a base-line of receptor activity. They were then treated with a 5 ml suspension of Detach (containing 1 g of granules), 30 min prior to a morning feed. Sampling was then continued for a further 48–72 h period.

Results:

About 1000 samples were collected in the three-day periods immediately before and after medications. Piglets were maintained on a milk diet. Many more samples were collected in the intermediate periods allowing a much ciearer, but basically similar pattern of receptor activity in vivo or be constructed.

Results of the sample collections made in both the periods immediately before and after Detach medication of the continuously sampled pigles are shown in Table 1. Postmedication reductions in receptor activity was observed, and these reductions were confirmed by one-way analysis of variance to be statistically significant ($P=0.05$) at 0–1 and 1–2 days after medication. This data supports previous observations of the disruptive influence of bromelain on the binding between various pathogen adhesions (including K88) and toxins and their intestinal receptors by in vitro experiments. It also provides evidence to support the hypothesis that it is the receptor-destroying capability of bromelain that confers the demonstrated ability of Detach to prevent various types of enteric infection.

Incidence of scours, treatments given and mortality were recorded to weaning.

Treatment, mortality and weight gain were also measured.

Results:

A summary of results up to weaning is given in Table 2.

TABLE 1

Continuously Sampled Piglets: K88 Receptor Activity in Intestinal Content Samples Collected Over Three Days Before or After Medication. Piglets were maintained on a milk diet during continuous sampling)

| Pig # | | K88 Receptor Activity* | | | |
|---|---|---|---|---|---|
| | | Pretreatment | | Post-Treatment | |
| | | (Days −3 to 0) | (Day 0–1) | (Day 1–2) | (Day 2–3) |
| 1 | DETACH | 0.71 ± 0.11 (21) | 0.19 ± 0.15 (16) | 0.33 ± 0.29 (40) | 0.17 ± 0.19 (15) |
| 1 | DETACH | 0.28 ± 0.14 (79) | 0.34 ± 0.21 (30) | 0.05 ± 0.10 (24) | |
| 2 | DETACH | 0.28 ± 0.22 (68) | 0.08 ± 0.08 (42) | 0.11 ± 0.15 (38) | 0.06 ± 0.09 (42) |
| 2 | DETACH | 0.55 ± 0.19 (39) | 0.11 ± 0.10 (25) | | |
| 3 | DETACH | 0.30 ± 0.17 (78) | 0.15 ± 0.10 (34) | 0.23 ± 0.20 (15) | 0.24 ± 0.24 (35) |

*Mean absorbance values obtained from the intestinal content samples when tested by KPEIA. Values shown in the table are mean absorbance (A540) ± standard deviation. The number of samples collected over each time period is indicated in brackets below the absorbance values.

EXAMPLE 4

Prophylactic control of diarrhoeal disease over a prolonged period (day 6 of life to weaning at about day 21).

A number of field trials have been conducted to demonstrate the efficacy of Detach treatment in prophylactic control of piglet diarrhoea. These trials have indicated that Detach treatment assists control of postweaning diarrhoea (which is associated commonly with K88+E. coli) using a single oral dose. In addition, Detach medication has been found effective in control of preweaner (Sucker) scouring diseases of piglets, again as a single oral dose. Preweaner scouring diseases are commonly associated with rotavirus or coccidial infections and usually are evident as chronic pasty diarrhoea commencing when the piglet is about 1 week of age and continuing for 1–3 weeks. Despite the more chronic nature of these diseases, a single dose of Detach given before the usual age at which onset of diarrhoea symptoms occur usually resulted in control of the diseases.

Methods:

The experimental farm was a commercial breeding unit located in central-western Victoria, Australia.

Gilts and sows were alternately allocated to Detach treated or control groups.

A total of 30 litters were used during this trial: 15 allocated to Detach and 15 to Control groups. Piglets were fostered at any time up to three days old, at which point every liter was weighed.

The Detach group piglets were dosed with a single oral dose of 5 ml Detach on day 6. The Control group were not treated with Detach.

Litters were again weighed at weaning on the day of transfer to the weaner accommodation.

TABLE 2

| | Results up to Weaning | | |
|---|---|---|---|
| Sows | Detach (+S.D.) | Control (+S.D.) | Significance |
| No. pigs/litter (day 3) | 9.87 (1.66) | 9.73 (1.16) | 0.745 |
| Pig wt. - day 3 (kg) | 1.66 (0.09) | 1.71 (0.15) | 0.532 |
| Mortality (scours) | 0.07 (0.26) | 0.07 (0.26) | 0.938 |
| Scour treatments/litter | 4.2 (1.93) | 22.67 (6.38) | <0.001 |
| Piglet weaning (kg) | 8.05 (0.45) | 5.97 (0.48) | <0.001 |
| Days to weaning | 30.00 (2.2) | 29.27 (1.67) | 0.41 |
| Weight gain to weaning | 6.38 (0.45) | 4.25 (0.54) | <0.001 |
| Daily liveweight gain | 213 (0.17) | 145 (19) | <0.001 |

The significance of the results was calculated by analysis of variance with piglets/litter and day 3 weight as co-variants where appropriate. Weaning ages were very similar, being based on management practices rather than pig performance. However, the other production criteria was highly significant as was the reduction in disease Treatment by 82%.

This trial clearly demonstrates the efficacy of a single dose of Detach in the prevention of preweaning scours. All the relevant criteria showed highly significant benefit from the treatment. Weaning weight was increased by 2 kg and disease treatments reduced by 80% in the treated litters. The lack of mortality made comparison on this parameter impossible.

Despite the short-acting nature of Detach pharmacologically, the advantage of an early dose of Detach appears to persist until weaning.

It appears from this trial that unless there is no clinical or performance evidence of preweaning scours, a single preweaning dose of Detach is a preferred management regime. The efficacy of Detach treatment against preweaning scours is clearly evident.

Five further rials have been carried out (data not shown) to assess the utility of the Detach treatment in preventing pre-weaner (sucker) scour. In these Trials, a 5 ml dose of Detach (according to Example 1) five days after birth was administered orally using a syringe. These trials clearly showed a clear reduction in pre-weaning scours as well as an additional benefit in post-weaning scours following weaning. Piglets treated with Detach also showed an increase weight gain, an overall improved health and reduction of disease.

Histological analysis of a number of control and treated piglets showed than a significant number of piglets were roravirus positive and Coccidial pathogens were found in post-mortem samples. In contrast, Detach treated piglets showed no such infection.

A number of additional trails were carried out to determine the effect of Detach in the prevention of post-weaner scours in piglets. A total of 1705 piglets were used in these trials of which 502 were negative controls, 100 were positive controls, 503 were dosed with 1 g of Detach in gel form (as per Example 1) and 600 were given alternative regimes of treatment. The efficacy of Detach was clearly shown in these investigations. No pigs dosed with a single dose of Detach died from *E. coli* scour. Only 2 pigs in the Detach regime died of scours compared with 16 control or antibiotic treated animals. In addition Detach was highly effective in reducing morbidity as measured by treatments given. Perhaps the most significant observation is the three-fold reduction in treatment necessary for post-weaning scour.

EXAMPLE 5

The role of enterotoxigenic *Escherichia coli* (ETEC) as an important eiologic agent in human diarrhoeal disease is well established (Sussman, M., The virulence of E. *coli*, Reviews of Methods. Soc. Gen. Micro., 1985). These organisms are characterised by their ability to produce one or both of a heat labile (LT) or heat stable (ST) enterotoxin (Gaastra, W. and de Graaf, F. K., Micro. Rev. 46: 129–161. 1982). Some strains also produce antigenic colonisation factors (CFA) or pill which permit adhesion of ETEC srains to the intestinal mucosa. These facilitate colonisation and allow enterotoxins to be delivered in close proximity to target epithelial cells (Gaastrs, et al., Supra).

This experiment describes the RITARD model of Spira et al. (Infect. Immun. 32: 739–747, 1981) to test the efficiency of the Detach formulation of Example 1 in vivo in reducing atachment of CFA/I positive *E. coli* to rabbit intestinal mucosa.

Materials and Methods:
Animals:

New Zealand White breed rabbits of both sexes from a single breeder were used for the experiment. Their weights ranged from 1.5 to 2.7 kg.

Bacteria:

ETEC strains used in this trial were originally isolated in Bangladesh from patients with diarrhoea. Strain H10407 (serotype 078:K88:Hll) and a mutant derivative of this strain, H10407p were kindly provided by D. C. Evans (Houston, Tex.) (Infect. Immun. 19: 727–736, 1978). Strain E1392/75 A (serope 06:K15:H16) was kindly provided by B. Rowe (London U.K.). Strain H10407 produces both ST and LT toxin and possesses the colonisation factor antipen CFA/I. H10407p produces boh ST and LT, however does not produce CFA/I. Strain E1392/75 7A is a non-pillared and non toxigenic spontaneous laboratory derivative of CFA/II *E. coli* 1392 (Sack, R. B. et al., Infect. Immun. 56: 378–394, 1988) and has been shown to neither colonise nor induce diarrhoea in the RITARD model (Wanke, C. A. e al., Infect. Immun. 55: 1924–1926, 1987).

Strains were inoculated onto CFA agar (Evans, Supra) and grown at 37° C. overnight. The bacteria were harvested, washed in serile phosphate buffered saline (0.01 M, pH 7.2: PBS) and diluted to desired optical desnity measurements. The bacterial concentration was also determined by viable cell count on duplicate blood agar plates after serial dilution in PBS. All cultures were checked for CFA/I and LT production by specific enzyme immunoassay (EIA) prior to rabbit inoculation.

RITARD Model:

The RITARD model developed by Spira et al. (Supra) was used, with slight modifications discussed below. Prior to challenge, half of the rabbits from each group (Table 1) were orally dosed with 0.42 g of the granular composition of Example 1, known as Detach, and starved for 18 hours, but were given water ad lithium.

Monitoring the Disease:

Rabbits were observed for diarrhoea, weakness or death hourly for the 24 hour post-challenge period. Rabbits were individually categorised with a diarrhoea score as 0, no diarrhoea; 1, mild diarrhoea with faeces softer than normal; 2, moderate diarrhoea with at least three watery stools; and 3, severe diarrhoea with multiple watery stools. Faecal swabs were collected when faeces were passed and rectal swabs were taken from rabbits not passing faeces. The challenge strains were identified by typical *E. coli* colony morphology and by EIA.

Collection of Tissue Specimens:

All animals were killed 24 hours post-challenge and the intraluminal fluid of the small intestine was measured. In euthanised or dead rabbits, large fluid volumes in the small intestine (>60 ml) was indicative that diarrhoea was a major contributor to death. Sections (2×3 cm) of small intestine were collected from five sites comprising, duodenal (S1), proximal jeiunum (S2), mid jejunum (S3), distal jeiunum (S4) and ileum (S5). Each segment was opened longitudinally and extensively washed in sterile PBS to determine strongly adherent bacteria, or left unwashed to determine total numbers present. Quantitative cultures were done by homogenising tissue for one minute using a Sorvall homogeniser at full speed. Serial dilutions were made in PBS and aliquots (25 µl) were plated onto blood agar and CFA agar. After incubation at 37° C. for 18 hours the number of bacteria per cm of tissue was determined. Other specimens were processed promptly for histology by fixation in 10% neutral buffered formalin. After the specimens were embedded in paraffin, both haematoxylin-eosin staining and tissue Gram staining were done.

Statistical Analysis:

Bacterial counts were log transformed to stabilise variances and analysed using Genstar 5. Efficacy of Detach protection was determined by Fortran-Finney, a program that determines efficacies (%) from chemotherapeutic tests (Finney, D. J., Statistical Method in Biological Assay, Pub. Charles Griffin and Company Ltd., 1952).

Results:

Groups of rabbits were given $1\times10^{11}$ bacteria of different *E. coli* strains and sterile PBS to observe the diarrhoeal response during a 24 hour incubation period. Results are shown in Table 3. Various *E. coli* enterotoxin and colonisation factor combinations were selected to include a piliated enterotoxigenic strain (H10407), an enterotoxigenic strain only (H10407p), and a non-pillared non-enterotoxigenic type (E1392/75/7A). A PBS control was included to observe the effect of surgery and Detach treatment without bacterial challenge.

None of the rabbits given 10 mls of sterile PBS developed diarrhoea. Neither did any of the rabbits challenged with non-pillared H10407p and E1392/75 7A. At autopsy, the fluid volumes in the small intestine from the pyloric sphincter to the ileocaecal junction ranged from 10–50 mls.

Of the eight control (non-Detach treated) rabbits challenged with H10407 seven died or had profuse water diarrhoea. At autopsy, the fluid volume in their small intestines ranged from 20–105 mls. The total volume in the small and large intestine combined, however, ranged from 130–165 mls (in comparison with 10–50 mls in rabbits inoculated with E1392/75 7A, H10407p and PBS).

Only one of the rabbits treated with Detach prior to H10407 challenge died. This rabbit died 11 hours post challenge after passing one loose stool. None of the other six rabbits treated with Detach had diarrhoea and the majority (4 of 6) had passed formed faeces by 24 hours. At autopsy, the contents of the large intestine were solid and the fluid accumulation in the small intestine ranged from 12–60 mls.

tinal flora which is depleted corresponds to pathogenic microorganisms. Such microorganisms may be replaced with advantageous microorganisms, such as those derived from healthy animals. Examples of such organisms, which may be referred to as "probiotics", may include streptococci and lactobacilli.

The number of bacteria bound to the small intestinal mucosa of rabbits infect with CFA/I⁻H10407p ranged from $1.3 \times 10^4$ CFU/cm (minimum count) to $6.6 \times 10^7$ CFU/cm in a rabbit with mild diarrhoea (mean $1.6 \times 10^7$ CFU/cm). Colonisation of CFA/II⁻ occurred at a similar level, with colonies (CFU/cm) ranging from $1.3 \times 10^4$ (minimum count) to $1.3 \times 10^{8,}$ mean=$3.9 \times 10^7$). There was no significant difference in bacterial numbers between Detach treated and non-treated animals challenged with either nonpiliated strain.

In rabbits that received sterile PBS only, relatively few bacteria were present in the small intestine (mean=$1.3 \times 10^4$ CFU/cm).

TABLE 3

Diarrhoeal Response in Rabbits Treated with or Without Detach and challenged with different ETEC Strains

| GROUP | STRAIN | ADHESIN | TOXIN | TREATMENT | DIARROEAL RESPONSE[a] |
|---|---|---|---|---|---|
| A | H10407[b] | CFA/I⁺ | ST⁺LT⁺ | D | 1/7[c] |
|   |   |   |   | C | 7/8[d] |
| B | H10704p | CFA/I⁻ | ST⁺LT⁺ | D | 1/4[e] |
|   |   |   |   | C | 1/4[e] |
| C | E1392/75 7A | CFA/II⁻ | ST⁻LT⁻ | D | 0/4 |
|   |   |   |   | C | 0/4 |
| D | PBS |   |   | D | 0/4 |
|   |   |   |   | C | 0/4 |

[a] = No. of animals with diarrhoea or death/total number tested.
[b] = Five rabbits omitted from analysis due to non diarrhoea related death.
[c] = Mild diarrhoea
[d] = Rabbit survived infection, colony counts at site 3 was $5.8 \times 10^9$.
[e] = Detach treated rabbit died, colony count at site 3 was $1.2 \times 10^7$.

Bacterial Adhesion:

Quantitative cultures were performed on all animals to study the adhesion of challenge bacteria in different parts of the small intestine. All samples were washed with sterile PBS to observe adherent bacteria to the gut mucosa. Challenge bacteria were apparent in all sites, with CFA/I⁺ H10407 strain being the most heavily colonised. Mean results of cultures done of CFA/I⁺ bacteria at various sites on non-Detach treated rabbits varied from lower values at S1, S2, S4 and S5 ($8.7 \times 10^{7,}$ $6.2 \times 10^{7,}$ $1.04$–$10^8$ and $6.2 \times 10^8$ colony forming units (CFU)/cm respectively) to consistently higher values at S3 ($6.2 \times 10^9$). Results are shown in Table 4. In the following analysis site 3 cultures were used for comparison.

The number of CFA/I⁺ bacteria adherent to the mucosa in the Detach treated rabbits ranged from $1.3 \times 10^4$ (minimum count) to $1.2 \times 10^7$ CFU/cm (means $2.6 \times 10^6$ CFU/cm). This represents over 2,000-fold less CFU/cm than the values for control rabbits challenged with the same strain (p<0.05). Table 4 illustrates the difference in colony counts between Detach treated and untreated animals.

It is clear from this Example that the Detach preparations significantly reduce intestinal flora. It is believed the intes-

TABLE 4

Mean Colonization of Small Intestine after RITARD Challenge With $10^{11}$ CFU Per Animal.

| GROUP | STRAIN | TREAT-MENT | COLONISATION |   |   |
|---|---|---|---|---|---|
|   |   |   | S1 | S3 | S5 |
| A | H10407 | D | $2.9 \times 10^6$ | $3.2 \times 10^6$ | $7.1 \times 10$ |
|   |   | C | $8.7 \times 10^7$ | $6.2 \times 10^9$ | $6.2 \times 10^8$ |
| B | H10407p | D | $1.0 \times 10^8$ | $2.3 \times 10^7$ | $1.2 \times 10^8$ |
|   |   | C | $1.9 \times 10^7$ | $1.2 \times 10^7$ | $1.8 \times 10^{10}$ |
| C | E1392/75 7A | D | $6.1 \times 10^6$ | $1.6 \times 10^7$ | $5.9 \times 10^6$ |
|   |   | C | $7.5 \times 10^6$ | $5.0 \times 10^7$ | $2.1 \times 10^{10}$ |
| D | PBS | D | $2.0 \times 10^6$ | $5.9 \times 10^5$ | $5.6 \times 10^5$ |
|   |   | C[a] | $3.2 \times 10^5$ | $1.3 \times 10^6$ | $1.2 \times 10^7$ |

[a] = excluding rabbit heavily colonised.

Fecal Excretion of Bacteria:

Fecal swabs were obtained from rabbits when faeces were passed. In all animals the challenge bacteria were excreted. Rectal swabs were taken at autopsy. Presence of the challenge strain in the rectum was apparent in all rabbits including those that had not passed faeces prior to termination of the experiment. In all instances, 100% of colonies cultured, were of the challenge strain.

Histology:

Histological studies of small intestinal tissues obtained from all rabbits revealed no mucosal abnormalities under light microscopy. Organisms were only rarely seen on the mucosa, suggesting that bacteria bound in certain areas, rather than an even distribution along the gut.

Discussion:

It is well known that there are gross similarities in mechanisms of pathogenesis between human and animal ETEC infections. Most ETEC strains of human and animal origin rely on pili for adhesion and subsequent colonisation of the small intestine. Also diarrhoeal disease in both species is elicited by the production of efficient delivery of enterotoxins.

In this experiment it is demonstrated that oral administration of Detach, a protease preparation, was successful in reducing diarrhoea and diarrhoea induced death by 86% (6 of 7) in rabbits infected with CFA/I positive H10407. 87% (7 of 8) of control rabbits receiving Detach died or suffered from severe diarrhoea.

Wanke, et al. (Supra) reported previously that the threshold for expression of clinical symptoms of diarrhoeal infection is $10^8$ CFU per cm of small intestine. In this study, rabbits challenged with bacterial strains possessing no known colonisation factors did not get diarrhoea and were colonised to levels below a threshold of $10^7$. In these rabbits there was no difference in levels of colonisation between the treatment groups. Alternatively, in non-Detach treated rabbits challenged with piliated H10407, bacteria colonised to levels well above $10^7$ (mean=$6.2\times10^9$). Detach treatment of rabbits, challenged with the same bacterial strain were only colonised to levels similarly observed with bacteria not possessing known CFA's (mean=$2.6\times10^6$). It is apparent therefore, that oral Detach treatment was successful in modifying the surface of the rabbit mucosa, such that colonisation of CFA/I$^+$ bacteria was significantly reduced ($p<0.05$).

These results obtained the rabbits are clearly extendible to human situation, given the gross similarities of pathogenesis between human and animal ETEC infections. Indeed, the rabbit is a standard model for the study of human bacterial infections.

The treatment of humans with the DeTach preparation should provide protection, for example, from enterotoxigenic *Escherichia coli* diseases. Such protection may arise from The degradation/modification of intestinal receptors for virulence determinants in human ETEC diarrhoea, such as colonisation factor antigens CFA/I, CFA/II, CFA/III and CFA/IV.

Experiments conducted by the applicant (data not shown) have shown that the treatment of human small intestine material with a protease (papain) results in extensive reduction in enterotoxigenic *Escherichia coli* bacterial adhesion, and in particular, reduced binding of CFA/I and enterotoxin To intestinal preparations, and complete inhibition of binding of CFA/II. This data is indicative that the Detach preparation should be effective in humans in-vivo, in providing protection from enterotoxigenic *E. coli* diseases.

EXAMPLE 6

Increased globulin levels follows Detach treatment.

This experiment was designed to duplicate human physiology using a pig model to determine The effect of large doses of Detach (>1 g) on serum biochemical parameters. A Ten fold dose rate was selected To investigate the change in serum globulin levels.

Experiment:

15 pigs 10–16 weeks of age were used for the experiment.

Group A—8 pigs untreated

Group E—7 pigs administered Detach (10 g) 3 times a day for 2 or 5 days.

Serum biochemical parameters pre-treatment and post-treatment in both groups were compared To observe any effects of the Treatment.

Results:

There appeared to be a significant ($p=0.043$) increase in serum globulin levels when pigs were treated with large doses of Detach. Lower doses of Detach (<10 g) did not result in any significant change (Data not shown).

Globulin levels were investigated further. Alpha, beta and gamma globulin levels were analysed by electrophoresis using cellulose acetate and quantitated by densitometer.

Results are set out in Table 5.

TABLE 5

| | Serum Globulin Levels | |
|---|---|---|
| Pig No. | Treatment | Increase Gamma |
| 225 | C | 1.41 |
| 204 | C | −0.24 |
| 202 | C | 1.32 |
| 242 | C | 0.04 |
| 240 | C | 0.28 |
| 219 | C | 2.21 |
| 203 | D | 2.16 |
| 228 | D | 2.53 |
| 224 | D | 1.51 |
| 217 | D | 1.22 |
| 214 | D | 2.06 |
| 238 | D | 4.07 |

The mean increase in gamma globulin is 170% Alpha and beta globulin levels varied be%ween pig samples, therefore no conclusions could be made. There was, however, a consistent increase in gamma globulin levels.

The changes in gamma globulin levels between pre-treatment and pos-treatment values in the wo groups were analysed by analysis of variance. This increase was statistically significant ($P=0.03$, 0–99.5%). The antigenic specificity (and antibody class) of the gamma globulins is yet to be determined.

These results show an increase in serum gamma globulin in what may be non-specific gamma globulin levels following detach administration. A rise in serum IgG may also have implications for mucosal immunity. This may provide an explanation for the broad antimicrobial spectrum of Detach which has been observed to be effective against bacterial, viral and protozoan infections.

EXAMPLE 7

Prevention of scours in calves.

A trial was carried out near Warragul in Victoria to assess the efficacy of Detach in preventing scours in young calves. The trial was carried out towards the end of the spring calving season in Gippsland where the main organism isolated from affected animals over the past few years has been Cryptosporidia.

The trial was carried out on six dairy farms. All these farms were "problem" farms where disease had been severe for several years.

Test Material: Detach according to Example 1. Dose: 35mL in the form of a gel.

Method:

The dose of Detach was 35 mL, repeated as required at about three to four day intervals. The maximum number of doses given to any calf was five.

In general, scouring occurred between one week and four weeks of age. Normally by 28 days the calves were moved from the rearing pens to the calf paddock and were less susceptible. Records were kept of scouring days, doses of antibiotics required and electrolytes given. Date of death was recorded, together with cause of death, where known. Faecal samples were sent to the laboratory for analysis. Intestinal samples were also forwarded from farms where mortalities occurred.

Calves were weighed on two farms at the end of the trial to try and gauge if there was a large different in growth rates between the two groups. No evidence of such a difference was obtained.

Data relating to number of scour days and antibiotic use per calf was analysed by paired + test. Mortality data was analysed by Chi-squared Test.

Trial and data results are summarised in Table 2.

TABLE 2

Summary of Detach Trial in Calves

|  | Treated | Control | P |
| --- | --- | --- | --- |
| Number of claves | 50 | 55 | |
| Mortality % | 4% | 25% | ** |
| Scour days per calf | 1.45 | 2.33 | ** |
| Doses of Detach per calf | 2.24 | — | |
| Antibiotic doses per calf | 0.34 | 1.00 | * |
| Electrolyte doses per calf | 2.98 | 3.18 | — |
| Average daily gain (kg/d) | 0.93[1] | 0.971 | — |
| Age of first scour (d) | 10.2 | 9.5 | — |

Notes:
[1]Calves weighed on two farms only
*P < 0.05
**P < 0.01

Detach significantly reduced mortality on almost every farm and also resulted in a reduced need for antibiotics and electrolytes. Death rate was reduced from 25% to 4%. (Different P<0.01). Antibiotic dosage was reduced from one dose per calf to 0.34 dose per calf. Electrolyte use was little changed with 3.18 doses given per control calf and 2.98 doses given per Treated calf. The number of days on which scouring was recorded was also reduced, from 2.33 days per calf in the control calves To 1.46 days per calf in The treated calves. (Difference P<0.01).

The biggest effect was on mortality. Mortality was sumably contributed by Cryptosporidia, the dominant pathogen isolated in faecal or post-mortem samples. Crytosporidia are a highly pathogenic intestinal parasite of young calves, for which there is no effective treatment available at present. Death may occur after only one or two days of scouring. In other cases the animal can be kept alive on electrolytes for several weeks in a very debilitated condition. Detach may offer real hope in treatment of this disease.

Two or more doses of Detach (35 mL) clearly protected young calves from Cryptosporidia infection and reduced the need for antibiotic therapy.

I claim:

1. A composition comprising:
   (i) granules comprising a biologically active material in association with a week base, the granules being partially coated with a delayed release material substantially impermeable at pH below about 6.0 and soluble in intestinal joice;
   (ii) an acidifying agent having a pH between about 1.5 to about 6 when in solution; and
   (iii) a gel forming agent.

2. The composition according to claim 1, wherein the biologically active material is a protein and is selected from the growth consisting of enzymes, growth factors and hormones.

3. The composition according to claim 2, wherein the protein is an enzyme selected from the group consisting of bromelin, papain, ficin, chymotrypsin, trypsin, ribonuclease, carboxypeptidate A, carboxypeptidate B, and subtilisin.

4. The composition according to claim 1, wherein the biological material is a non-proteinaceous biological material.

5. The composition according to claim 4, wherein the non-proteinaceous biological material is selected from the group consisting of vitamins, co-factors, metal ions and antibiotics.

6. The composition according to claim 1, wherein the gel forming agent forms a gel when mixed with a solvent.

7. The composition according to claim 1, wherein from 10 to 90% of the surface area of the granules is coated with the delayed release material.

8. The composition according to claim 1, wherein the acidifying agent is in particulate form.

9. The composition according to claim 1, wherein an acidic gel containing microgranules forms on the addition of an aqueous solution to the composition.

10. The composition according to claim 1, further comprising an antibiotic.

11. A composition comprising:
    an acidic gel having a pH between about 1.5 to about 6; and
    microgranules comprising a biologically active material in association with a weak base, the microgranules being partially coated with a delayed release material substantially impermeable at pH below about 6.0 and soluble in intestinal juice.

12. The composition according to claim 11, wherein the biologically active material is a protein and is selected from the growth consisting of enzymes, growth factor, and hormones.

13. The composition according to claim 12, wherein the protein is an enzyme selected from the group consisting of bromelin, papain, ficin, chymotrypsin, trypsin, ribonuclease, carboxypeptidate A, carboxypeptidate B, and subtilisin.

14. The composition according to claim 11, wherein the biological material is a non-proteinaceous biological material.

15. The composition according to claim 14, wherein the non-proteinaceous biological material is selected from the group consisting of vitamins, co-factors, metal ions and antibiotics.

16. The composition according to claim 11, wherein from about 10 to about 90% of the surface area of the microgranules is coated with the delayed release material.

17. The composition according to claim 11, further comprising an antibiotic.

18. A method for the delivery of a biologically active substance to the upper small intestinal tract of an animal, the method comprising:
    reacting the composition of claim 1 with a solvent to form a gel: and
    orally administering the gel to the animal.

19. A method for the delivery of a biologically active substance to the upper small intestinal tract of an animal, the method comprising orally administering to the animal a composition according to claim 10.

20. A method for the treatment of intestinal pathogens and diseases associated with intestinal pathogen infection in an animal, the method comprising:

reacting the composition of claim 1, wherein said biologically active material is a protease, with a solvent to form a gel; and orally administering the gel to the animal.

21. A method for the treatment of intestinal pathogens and diseases associated with intestinal pathogen infection in an animal the method comprising orally administering the animal a therapeutically effective mount of a composition according to claim 11, wherein said biologically active material is a protease.

22. A method according to claim 20 wherein said protease is bromelin.

23. The method according to claim 20, wherein said intestinal pathogen is selected from the group consisting of bacteria, viruses, and parasites.

24. The method according to claim 23, wherein said intestinal pathogen is selected from the group consisting of enterotoxigenic *Escherichia coli*, Shigella, Yersinia, Pleisiomonas, Vibrios, Aeromonas, Campylobacter, rotavirus, Cryptosporidia and Coccidosis.

25. The method according to claim 20 wherein said composition further comprises an antibiotic.

26. The method according to claim 20, wherein the administering comprises administering an antibiotic.

27. The method according to claim 20, wherein said animal is a monogastrate or immature ruminant.

28. The method according to claim 20, wherein said animal is selected from the group consisting of humans, pigs, calves, horses, fish and crustacea.

29. A method for the treatment of diarrhoea in an animal comprising administering to the animal an acidic gel having a pH between about 1.5 to about 6, said gel containing microgranules comprising a proteolytic enzyme in association with a weak base, the microgranules being partially coated with a delayed release material soluble in intestinal juice but substantially impermeable at a pH below about 6.0.

30. The method according to claim 29, wherein said proteolytic enzyme is bromelin.

31. The method according to claim 21, wherein said gel comprises an antibiotic.

32. A method according to claim 29, wherein the administering comprises administering an antibiotic.

33. A method for the non-specific stimulation of the immune system of an animal, comprising:

reacting the composition of claim 1, wherein said biologically active material is a protease, with a solvent to form a gel; and orally administering the gel to the animal.

34. A method for the non-specific stimulation of the immune system of an animal, comprising:

orally administering to the animal a composition according to claim 10 wherein said biologically active material is a protease.

35. The method according to claim 33, wherein said protease is bromelin.

36. The method according to claim 33, wherein the animal is selected from the group consisting of humans, pigs, calf, horses, fish, and crustacea.

37. A method of using a composition according to claim 1, wherein the biologically active material is a protease, the method comprising preparing a medicament for treatment of intestinal pathogens or diarrhoea in animals.

38. The method of claim 37, wherein the protease is bromelin.

* * * * *

UNITED STATES PATENT AND TRADEMARK OFFICE
CERTIFICATE OF CORRECTION

PATENT NO. : 5,484,609                      Page 1 of 5
DATED : January 16, 1996
INVENTOR(S) : T.S.Y. Ko It is certified that error appears in the above-indentified patent and that said Letters Patent is hereby corrected as shown below:

| COLUMN | LINE | |
|---|---|---|
| 1 | 9 | "animals, is" should read --animals is-- |
| 1 | 64 | "%he" should read --the-- |
| 2 | 34 | "Types" should read --types-- |
| 2 | 57 | "sored" should read --stored-- |
| 2 | 64 | "he" should read --the-- |
| 3 | 48 | "*coli* Shigella," should read --*coli*, Shigella-- |
| 4 | 2 | "he" should read --the-- |
| 4 | 23 | "status the" should read --status, the-- |
| 4 | 33 | "To" should read --to-- |
| 4 | 36 | "The" should read --the-- |
| 4 | 36 | "The" should read --the-- |
| 4 | 46 | "no" should read --not-- |
| 4 | 47 | "anibiotics," should read --antibiotics,-- |
| 5 | 35 | "The" should read --the-- |

UNITED STATES PATENT AND TRADEMARK OFFICE
CERTIFICATE OF CORRECTION

PATENT NO. : 5,484,609
DATED : January 16, 1996
INVENTOR(S) : T.S.Y. Ko

It is certified that error appears in the above-indentified patent and that said Letters Patent is hereby corrected as shown below:

| COLUMN | LINE | |
|---|---|---|
| 5 | 46 | "The" should read --the-- |
| 5 | 46 | "The" should read -the-- |
| 5 | 52 | "This" should read --this-- |
| 5 | 60 | "o 500" should read --to 500-- |
| 5 | 61 | "%he" should read --the-- |
| 5 | 62 | "he" should read --the-- |
| 5 | 62 | "he" should read --the-- |
| 6 | 49 | "1" should read --1.-- |
| 6 | 51 | "2" should read --2.-- |
| 6 | 54 | "3" should read --3.-- |
| 6 | 54 | "2,5" should read --2.5-- |
| 6 | 59 | "4" should read --4.-- |
| 6 | 62 | "5" should read --5.-- |
| 7 | 14 | "waer" should read --water-- |
| 7 | 16 | "ramked" should read --ranked-- |

UNITED STATES PATENT AND TRADEMARK OFFICE
CERTIFICATE OF CORRECTION

PATENT NO. : 5,484,609
DATED : January 16, 1996
INVENTOR(S) : T.S.Y. Ko

It is certified that error appears in the above-indentified patent and that said Letters Patent is hereby corrected as shown below:

| COLUMN | LINE | |
|---|---|---|
| 7 | 42 | "3ng" should read --2ng-- |
| 7 | 43 | "bu" should read --but-- |
| 7 | 44 | After "titration." and before "Residual" insert paragraph. |
| 7 | 44 | "bromelain" should read --bromelin-- |
| 7 | 46 | "Bromelain" should read --Bromelin-- |
| 8 | 6 | "DeTach" should read --Detach-- |
| 9 | 1 | "bromelain" should read --bromelin-- |
| 9 | 12 | "Piglets" should read --(Piglets-- |
| 9 | 61 | "liter" should read --litter-- |
| 10 | 53 | "Treatment" should read --treatment-- |
| 11 | 3 | "rials" should read --trials-- |
| 11 | 14 | "than" should read --that-- |
| 11 | 18 | "trails" should read --trials-- |
| 13 | 30 | "ST$^{LT-}$" should read --ST·LT-- |
| 15 | 43 | "DeTach" should read --Detach-- |

UNITED STATES PATENT AND TRADEMARK OFFICE
CERTIFICATE OF CORRECTION

PATENT NO. : 5,484,609
DATED : January 16, 1996
INVENTOR(S) : T.S.Y. Ko

It is certified that error appears in the above-indentified patent and that said Letters Patent is hereby corrected as shown below:

| COLUMN | LINE | |
|---|---|---|
| 15 | 55 | "To" should read --to-- |
| 15 | 64 | "The" should read --the-- |
| 15 | 66 | "Ten" should read --ten-- |
| 15 | 66 | "To" should read --to-- |
| 16 | 7 | "To" should read --to-- |
| 16 | 8 | "Treatment." should read --treatment.-- |
| 16 | 36 | "be%ween" should read --between-- |
| 16 | 40 | "pos-treatment" should read --post-treatment-- |
| 16 | 40 | "wo" should read --two-- |
| 17 | 31 | "0.971" should read --$0.97^1$-- |
| 17 | 43 | "Treated" should read --treated-- |
| 17 | 45 | "The" should read --the-- |
| 17 (Claim 1, | 62 line 3) | "week" should read --weak-- |

UNITED STATES PATENT AND TRADEMARK OFFICE
CERTIFICATE OF CORRECTION

PATENT NO. : 5,484,609

DATED : January 16, 1996

INVENTOR(S) : T.S.Y. Ko

It is certified that error appears in the above-identified patent and that said Letters Patent is hereby corrected as shown below:

| COLUMN | LINE | |
|---|---|---|
| 18 (Claim 12, | 37 line 3) | "factor," should read --factors,-- |
| 19 (Claim 21, | 62 line 3) | "administering the" should read --administering to the-- |
| 20 (Claim 36, | 62 line 2) | "calf," should read --calves,-- |

Signed and Sealed this

Ninth Day of July, 1996

*Attest:*

BRUCE LEHMAN

*Attesting Officer*   *Commissioner of Patents and Trademarks*